United States Patent [19]

Kolodziej

[11] 4,240,296
[45] Dec. 23, 1980

[54] MEASUREMENT OF TORSIONAL ACCELERATION OF A ROTATING BODY

[75] Inventor: Robert M. Kolodziej, Varysburg, N.Y.

[73] Assignee: Joy Manufacturing Company, Pittsburgh, Pa.

[21] Appl. No.: 70,283

[22] Filed: Aug. 27, 1979

Related U.S. Application Data

[63] Continuation-in-part of Ser. No. 944,526, Sep. 21, 1978, abandoned.

[51] Int. Cl.³ .............................................. G01P 15/09
[52] U.S. Cl. .................................... 73/650; 73/517 A
[58] Field of Search ................ 73/649, 650, 652, 654, 73/658, 660, 517 A

[56] References Cited

U.S. PATENT DOCUMENTS

| 2,638,556 | 5/1953 | Hausz . | |
|---|---|---|---|
| 2,650,991 | 9/1953 | Ketchledge . | |
| 2,726,074 | 12/1955 | Ketchledge . | |
| 3,101,003 | 8/1963 | Lees . | |
| 3,791,203 | 2/1974 | Rice | 73/650 |
| 3,854,340 | 12/1974 | Bell et al. | 73/517 R |
| 3,893,342 | 7/1975 | Florian et al. | 73/517 R |

OTHER PUBLICATIONS

"Torsiona Response of Compressor Shaft Systems during Synchronous Motor Startup", Parts I, II & III by Mruk et al., ASME Publications–papers presented 9–1977.

Primary Examiner—James J. Gill
Attorney, Agent, or Firm—George Patrick Baier

[57] ABSTRACT

A device is provided for measuring the torsional acceleration of a rotating body, and particularly for measurement of oscillatory torques such as the starting torque of a synchronous motor. The device consists of two identical accelerometers mounted on a rotating body at equal radii 180° apart, and oriented so as to be insensitive to the outwardly directed radial forces present during acceleration.

6 Claims, 5 Drawing Figures

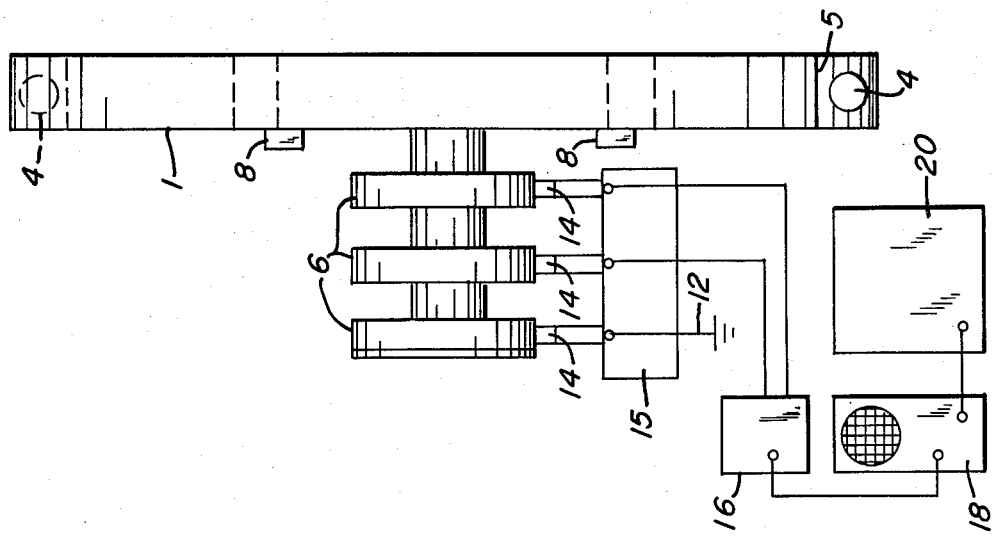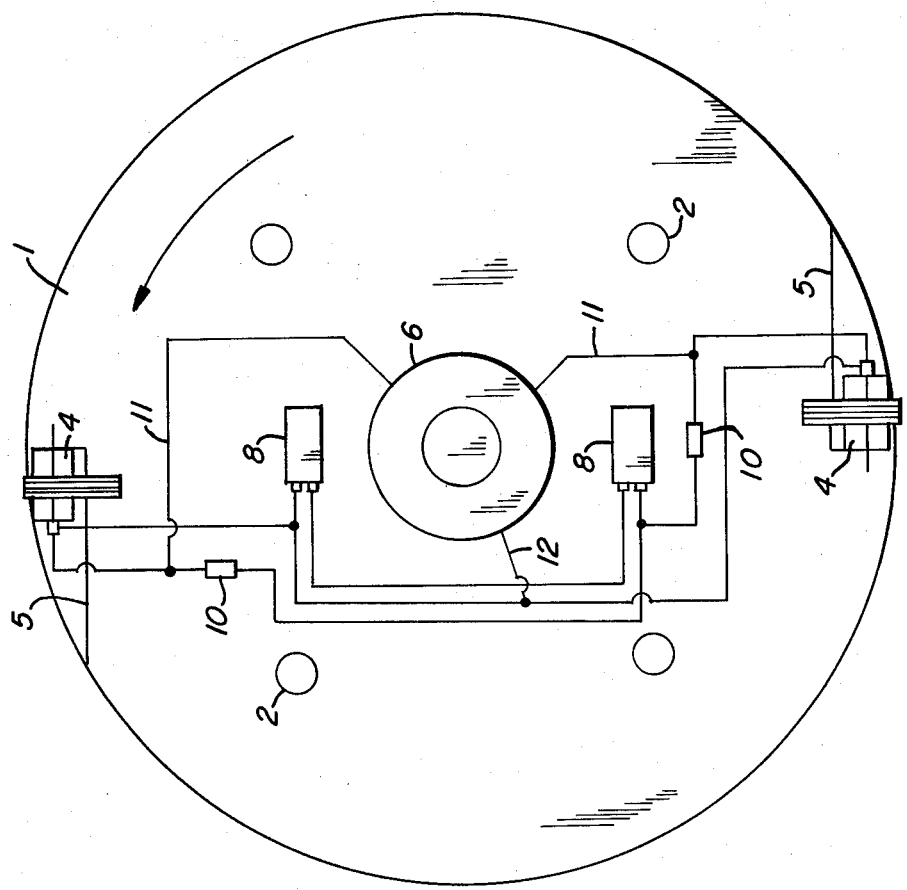

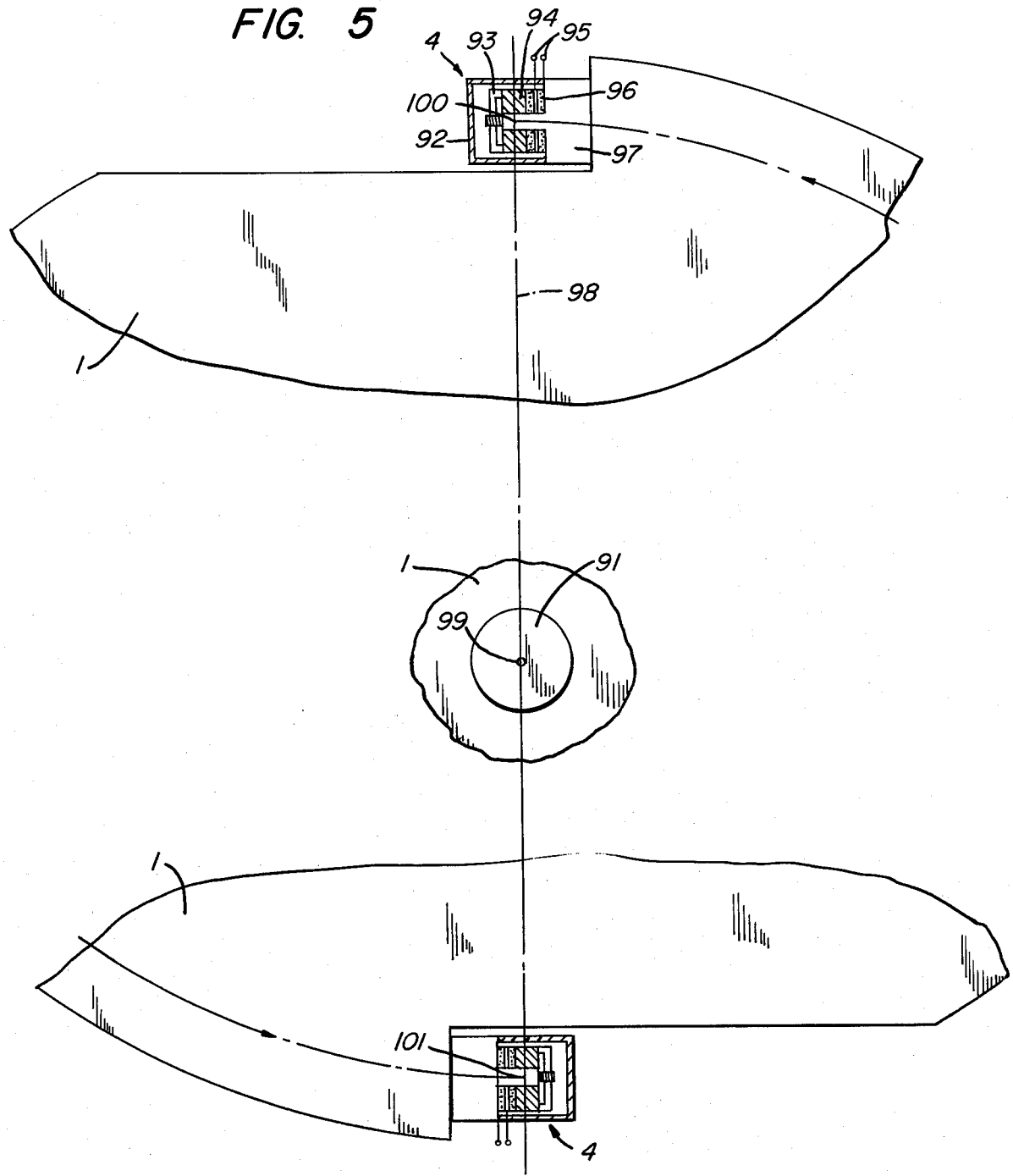

MEASUREMENT OF TORSIONAL ACCELERATION OF A ROTATING BODY

This is a continuation-in-part of application Ser. No. 944,526 filed Sept. 21, 1978, now abandoned.

BACKGROUND OF THE INVENTION

The present invention relates to means for the measurement of torsional or rotational acceleration of a rotating body such as a shaft, and more particularly to the measurement of oscillatory starting and accelerating torques in rotating machines such as synchronous motors.

Synchronous motors are widely used for many types of drives because of their good efficiency and constant speed as well as the ability to provide power factor correction. The use of a synchronous motor, however, presents certain problems in the design of the driven system because of the nature of the starting torque of such motors. A synchronous motor, as such, has no starting torque and these motors are normally started as induction motors. The direct current field excitation is then applied when the speed approaches synchronism so that the motor pulls into step and runs at synchronous speed. Such motors are almost always of salient pole construction and the airgap torque during initial operation as an induction motor is, therefore, pulsating or oscillatory. When starting from standstill, the frequency of oscillation is initially twice the line frequency, and decreses to zero as the motor accelerates and finally pulls into synchronism, when the torque reaches a steady-state value. Thus, during the starting period, a range of frequencies extending from zero to twice the line frequency occurs and any natural resonant frequencies of the load or driven system in this range may be excited during this start-up period leading to undesirable and excessive vibration. The motor starting torque characteristics and the torsional response of the driven system can be analytically determined in many cases, but it is often desirable to make actual measurements of the magnitude and frequency of oscillation of the motor torque during the starting period, so that the design of the driven system can be properly coordinated with the motor characteristics and undesirable resonance and vibration problems avoided.

SUMMARY OF THE INVENTION

The present invention provides a convenient and accurate means for measuring the torsional acceleration of a rotating shaft which, in the case of a motor which is not coupled to a load, is a direct measure of the accelerating torque of the motor.

In accordance with the invention, the desired measurement is made by means of two identical piezoelectric accelerometers mounted at equal radii and 180° apart on a rotating body whose acceleration is to be measured. The accelerometers are oriented in such a position that their maximum sensitivity is in the tangential direction. Consequently, the direction of minimum or zero sensitivity is radial, so that the measurement is not affected by radial forces. The accelerometers thus measure the tangentially directed forces to which they are subjected and provide output signals representing the tangential or torsional acceleration. The signals from the two accelerometers are taken from the rotating body by slip rings, or other suitable means, and the two signals are summed and observed or recorded in any desired manner. The use of two diametrically-opposed accelerometers makes it possible to add their signals which has the effect of cancelling out gravitational effects while doubling the desired signal representing the acceleration. Since the accelerating torque of a synchronous motor is proportional to the rotational acceleration, the signal obtained represents the airgap torque of the motor and the magnitudes and frequency of the oscillatory torques can readily be determined.

BRIEF DESCRIPTION OF THE DRAWINGS

The invention will be more fully understood from the following detailed description, taken in connection with the accompanying drawings, in which:

FIG. 1 is a view, in elevation, of a torque measuring device embodying the invention;

FIG. 2 is a side view of the device of FIG. 1;

FIG. 5 is a fragmented elevational view of an embodiment having the sensors 4, mounted on disc 1 in an alternate position from that shown in FIG. 1.

DESCRIPTION OF THE PREFERRED EMBODIMENT

Figure 3:
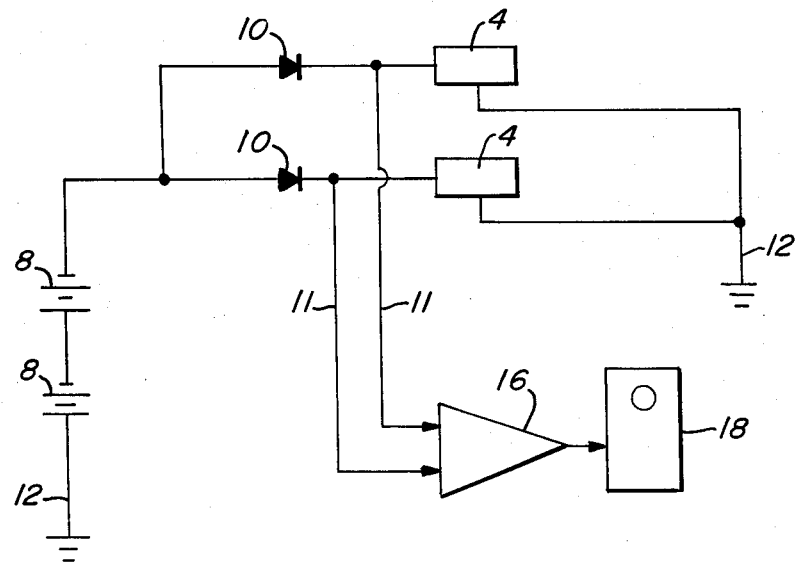
FIG. 3 is a schematic diagram showing the circuit of the device.

As shown in the drawing, the acceleration measuring device includes a rotating disc member or support 1. The support 1 may represent a shaft or other rotating body to be monitored but preferably is a separate disc as shown in the drawing which is adapted to be mounted coaxially on a shaft, a motor rotor, or other rotating body, for rotation therewith. The disc may be made of steel or other rigid material, and suitable mounting holes 2 may be provided. The measurement is made by means of two identical accelerometers 4 mounted on the disc 1. The accelerometers 4 may be of any suitable type and have not been shown in detail as their construction is not a part of the invention. The accelerometers 4 are preferably ceramic piezoelectric accelerometers and should be closely matched, that is, they should be substantially identical. Such accelerometers utilize the piezoelectric effect of a ceramic material, usually in the form of a beam which is deflected by the force to be measured to provide an electrical output signal. In this case, the tangential acceleration of the disc 1 is to be measured. For this purpose, two recesses or notches 5 are formed in the periphery of the disc 1 at diametrically-opposite positions, and the accelerometers 4 are mounted in the recesses 5 exactly 180° from each other and at equal distances from the axis of rotation of the disc. Piezoelectric accelerometers have a sensitive axis, or axis of maximum sensitivity, and the accelerometers 4 should be postioned so that this axis is tangential with respect to the disc 1 so as to be subjected to the tangential force, which corresponds to the torsional acceleration. Similarly, such accelerometers have a zero axis, or axis of minimum sensitivity, and the accelerometers must be positioned so that this minimum sensitivity axis extends in the radial direction so that the output signals are not affected by the radial or centrifugal forces to which the accelerometers are subjected.

Each of the accelerometers 4 produces an electrical output signal representing the tangential force or acceleration to which it is subjected. In accordance with the invention, the signals from the two accelerometers are summed, which doubles the sensitivity and correspondingly increases the signal representing the accelerating force, and which also have the effect of cancelling out the gravitational forces which affect both accelerometers on each revolution. Since these forces are equal and oppositely directed with respect to the two accelerometers, addition of the output signals cancels them out. The signals from the accelerometers may be transmitted from the rotating disc 1 to the stationary location in any suitable manner. As shown in the drawing, slip rings 6 are preferably used for this purpose. These may be copper slip rings of any suitable type mounted on the axis of the disc 1 as shown in FIG. 2 to rotate therewith.

The complete measuring circuit may be of any suitable type. In the arrangement shown in the drawing, energy for the accelerometers is supplied by battery cells 8 which are connected in series and mounted on opposite sides of the axis of the disc 1 so as to be mechanically balanced. The battery cells 8 are connected to the accelerometers 4 through constant current diodes 10 to insure constant sensitivity of the accelerometers over a range of battery voltages. Each accelerometer is connected to one of the slip rings 6 by a lead 11 while the other terminals of the accelerometers, and the opposite terminal of the battery, are connected to the third slip ring for connection to an external ground 12. Stationary brushes 14 engage the slip rings 6 to pick up the signals from the rotating disc 1. Any suitable type of brush support and pickup device 15 may be provided. The signals from the accelerometers 4 are thus transmitted to a stationary location, which may be remote from the disc 1 if desired, and are applied to a summing amplifier 16. The signals from the two accelerometers are added in the amplifier 16 and may be amplified as necessary for observation and recording. Any suitable means may be used for observing the signals. As shown in FIGS. 2 and 3, an oscilloscope 18 of any desired type may be connected to the amplifier 16 to provide a visual display of the torque characteristic which an be photographed or otherwise recorded and, if desired, a real time analyzer or tape recorder 20 of any suitable type may also be provided to make a permanent record which can be studied and analyzed as desired.

Figure 4:
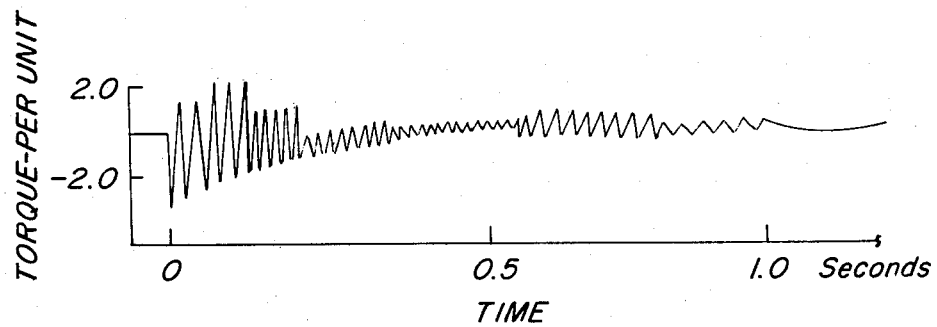
FIG. 4 is a diagram showing a typical motor torque measurement.

The type of test record or data obtainable with this device is shown by way of example in the curve of FIG. 4, which shows the instantaneous airgap torque of a typical synchronous motor during the starting period. As there shown, the starting torque is oscillatory and the oscillations are initially at twice line frequency and of substantial magnitude. As the motor accelerates, the amplitudes change and the frequency of oscillation decreases until it finally falls to zero when synchronous speed is reached at the end of the starting period and the torque reaches its steady-state value. A curve of this kind shows very clearly the magnitudes and frequencies of the torques produced during the starting period, and study of such a curve makes it possible to design the load or shaft system to be driven by the motor in such a way that no natural resonant frequencies occur close to the oscillatory frequencies to the expected during starting and especially in regions where the torque pulsations may be high. The design of a complete synchronous motor drive is thus greatly facilitated and undesirable resonance and vibration problems can be avoided.

The method and apparatus as previously described in this application functions for measuring the torsion acceleration of a rotating body and can be used to measure the oscillatory torques such as the starting torque of a synchronous motor. However, for accurate measurement of the oscillatory torques over a range of speeds during a period of acceleration such as, for example, the start up period of a synchronous motor, a more accurate apparatus and method is desired. During periods of rapid acceleration it has been found that centrifugal forces on the piezoelectric accelerometer can cause the unit to saturate and give erroneous readings. It is desirable to use an apparatus which does not subject the piezoelectric accelerometer to the high centrifugal forces such forces being several hundred times the acceleration of gravity present during the start-up period of a rotating machine. The apparatus shown in FIG. 5 solves these problems and accurately measures oscillatory torques without interference from the high centrifugal forces exerted on the accelerometer during the starting period. FIG. 5 is an elevational view of a torque measuring device similar to that shown in FIG. 1, but having two identical piezoelectric elements 4 arranged within the corresponding recesses in the disc 1 in a manner so as not to be influenced by centrifugal forces exerted on the piezoelectric sensors 4. FIG. 5 shows a fragmented view of a disc 1 having upper, lower and center portions. The disc 1 is mounted on a shaft 91. The shaft 91 and disc 1 rotate about a common center or axis of rotation 99. Two piezoelectric sensors 4 are mounted diametrically opposite along the center line 98. The piezoelectric sensors 4 are shown in partial cross section; and have an outer housing 92 and a base portion 97 which secures the piezoelectric sensor 4 to the disc 1. In contrast to the mounting arrangement shown in FIG. 1, the piezoelectric element is mounted such that the center of mass 100 of the mass in the upper piezoelectric sensor 4, and the center of mass 101 of the mass. 101 in the lower sensor element 4 are mounted diametrically opposite each other, and along a line containing the center of rotation 99 of the disc 1. The center of rotation 99 would normally correspond to the axis of rotation of the shaft of the rotating apparatus being measured.

Further detail of the piezoelectric sensor 4 is shown in the upper portion of FIG. 5, and it is to be understood that the lower sensor element 4 shown in FIG. 5 has identical respective parts. The sensor 4 has an outer housing 92 which is secured to the recess in the disc 1. Within the housing 92 is a rigidly fixed base portion 97. Contacting the base portion 97 are a group of crystals or other piezoelectric sensing material 96. Adjacent to and bearing upon the crystal 95 is a mass 94 which has a center of mass or gravity shown at position 100. In the particular embodiment shown in FIG. 5 the piezoelectric crystal member 96 is preloaded by means of a tensioning spring 93 which at all times maintains a constant forcible contact between the mass 94 and the sensor material 96 at the respective interfacing surface. The particular piezoelectric sensing element 4 shown in FIG. 5 is well known. It is typical of piezoelectric accelerometers which use a mass to act upon a piezoelectric material which produces an electrical output in response to acceleration forces exerted on the piezoelectric material by the mass. In the embodiment shown in FIG. 5 output terminals 95 are connected to the piezoelectric material 96 to provide means for connecting the electrical output of sensors 4 into a circuit such as shown in FIG. 3.

As is apparent from the geometric relationship shown in FIG. 5 of the centers of mass 100, 101 of the mass elements 94 that as the disc 1 undergoes changes in radial velocity the mass elements 94 exert only tangential forces on their respective piezoelectric elements 96. This results from the relationship of the center of mass and the plane of the interface between the mass 94 and the piezoelectric elements 96. As can be seen in FIG. 5 the plane of the interface between piezoelectric elements 96 and the mass 94 is parallel to the line 98. Because the output from terminals 95 is most highly responsive to forces exerted perpendicular to the plane of the interface surface between the mass 94 and the piezoelectric elements 96, the sensors 4 mounted as shown in FIG. 5 will not be responsive to forces on the mass 94 which are directed radially outward.

The cross-section of the sensors 4 in FIG. 5 shows the interface between the mass 94 and the piezoelectric material 96, lying in a plane generally parallel to the line formed by the upper center of gravity or mass 100, the point 99 along the axis of rotation, and the lower center of gravity or mass 101. In the piezoelectric sensor 4 shown in the embodiment of FIG. 5 the mass 94 and pizeoelectric material 96 is in the form of cylindrical disks having central axial bores which are operably mounted on the base 97. Other piezoelectric sensor structures having a signal responsive to an external force exerted on the crystal in the direction perpendicular to the plane of the interface between the crystal and the mass are included in my invention.

As described above, the apparatus in FIG. 5 positions the interface plane between the mass 94 and crystal 96 in both sensors 4 parallel to the line 98 connecting the centers of mass 100 and 101 of respective mass elements 94. Such positioning allows the apparatus to be generally non-responsive to the outward radial forces present during an acceleration of the shaft 91 and disc 1. In addition in applications where the disk is subjected to vibration in an axial direction, the interface plane formed between the mass 94 and crystal material 96 in each sensor element should be in a plane parallel to the plane defined by the axis of rotation and the line 98 so the sensors 4 are generally insensitive to the axial vibration in the disc 1.

Piezoelectric accelerometers are most responsive to forces exerted perpendicular to the interface surface, and least responsive to forces exerted generally parallel to the interface surface. By mounting the sensor 4 as described above the radial forces are acting generally parallel to the crystal interface, and therefore have a reduced contribution to the output signal at terminals 95. In actual piezoelectric accelerometer construction there is a direction in the plane of the interface that yeilds a zero electrical output in response to forces exerted on the crystal along that direction. That direction is the zero-cross axis of the accelerometer. By experiment it has been found that the zero-cross axis can be determined by the use of a shaker table to move the accelerometer while observing the electrical output. The cross axis is then related to the orientation of the accelerometer housing. By positioning the accelerometers on the disc 1 as described above such that the zero-cross axis of each accelerometer is directed generally radially outward the output signals are insensitive to radial forces.

Because the disc is subjected to torsional impulses during changes in radial velocity, a certain amount of undesirable torsional vibrations are generated within the disc 1 itself. When measuring the torsional acceleration of a synchronous motor during a starting period a broad band of undesirable frequencies of generated vibration is created within the disc. Such range of frequency will include the frequency of the inherent diametrical, umbrella, and tangential modes of vibration of the disc as the machine is accelerated from zero speed up to synchronous line speed. These generated torsional vibrations within the disc are undesirable during an analysis of the torsional acceleration because the distortion signals must be separated before an accurate signal corresponding to torsional acceleration of the disc can be determined. In addition, as the output signal of the piezoelectric sensor is generally a squared function of the frequency of the acceleration, the higher order distortion signals can cause the accelerometer to saturate during the high acceleration rates experienced in starting a synchronous motor. The distortion signals can be reduced or minimized so as to be insignificant by the use of a material such as laminated paper phenolic or plastic in the construction of the disc 1. When the disc is made of such a material having good vibration dampening qualities the output signal from the piezoelectric sensors 4 is generally free of any distortion resulting from resonant frequencies generated due to the geometry of the disc 1.

It should now be apparent that a device has been provided for monitoring the torsional acceleration or airgap starting torque of a synchronous motor, or other rotating device, in a relatively simple but highly accurate manner. The device shown can, of course, be a separate instrument as described or could be permanently attached to a rotating shaft or other member for use as an acceleration monitor during service. It will be undertood that any suitable type of accelerometers can be used in the manner described and may be connected in any desired manner to sum their signals. Also, devices can be used which will produce a velocity, rather than acceleration, signal; and this velocity signal then differentiated to produce an acceleration signal. Accordingly, as used in the following claims, "acceleration measurement device" means either a device for producing an acceleration or a device for producing a velocity signal which is then differentiated. The use of slip rings is a convenient and desirable manner of transmitting the signals from the rotating disc, but any other means such as telemetry equipment might be used, if desired.

I claim:

1. A method of determining the values of acceleration torque over a range of speeds of a rotating member comprising:

mounting on a structure having vibration dampening characteristics a material pair of accelerometers each having a mass member contacting a piezoelectric member at a planar interface surface and an electrical output signal representative of the force exerted on said piezoelectric member by said mass in a direction perpendicular to said interface surface for rotation with such rotating member generally 180° about the axis of rotation of said rotating member;

positioning said accelerometers generally tangential to the rotation of such rotating member and such that the centers of mass of both of said mass members lie on a line with and generally equally spaced from the center of rotation of said rotating member;

further positioning said accelerometers such that each of said interface surfaces are parallel to such line;

summing the output signals of said accelerometers; and accelerating said rotating member over a range of rotational velocities while analyzing such sum as representative of the acceleration torque of such rotating member as a function of speed.

2. The methods of determining the values of acceleration torque of claim 1 further comprising:
further positioning said accelerometers such that said interface surfaces are upon opposite sides of and parallel to the plane formed by such line and the axis of rotation of such rotating member, and further positioning the zero-cross axis of each of said accelerometers in a generally outwardly radial direction.

3. The method of claim 1 wherein said accelerating is over a range of rotational velocities generally extending from zero to the synchronize speed of a synchronous motor.

4. The method of claim 1 further including the storing of said sum and analyzing such stored sum after said rotating machine has accelerated through said speed range.

5. An apparatus for measuring the torsional acceleration of a rotating member over a range of speeds comprising:
a first accelerometer having a first mass member forcibly contacting a crystal member at a first planar interface surface such first accelerometer having a first electrical output signal representative of the external forces applied to said first mass;
a second accelerometer having a second mass member forcibly contacting a crystal member forming a second planar interface surface such second accelerometer having a second electrical output signal representative of the external forces acting on such second mass;
means for mounting said first and second accelerometer for rotation with said member about the axis thereof at diametrically opposite positions about such axis generally 180° apart such that the center of mass of said mass members of the respective accelerometers are generally equidistant about the axis of said rotating member and positioned 180° apart such that the center of mass of the first mass and the center of mass of the second mass and the center of rotation of said accelerometers forms a line, said accelerometers positioned such that said first interface surface and said second interface surface are parallel to said line;
said mounting means being of a material having vibration dampening characteristics;
means for summing the output signals of said first and second accelerometer; and
means for analyzing the sum of said output signals as a function of the rotation velocity of said rotating member over a range of speeds.

6. The apparatus of claim 5 wherein said mounting means includes means for positioning said first interface surface and said second interface surface opposite sides of and parallel to the plane formed by such line and the axis of rotation of such rotating member; and means for positioning the zero-cross axis of each of said accelerometers in a generally outwardly radial direction.

* * * * *